United States Patent [19]

della Valle et al.

[11] Patent Number: 4,716,223

[45] Date of Patent: * Dec. 29, 1987

[54] METHOD FOR PREPARING GANGLIOSIDE DERIVATIVES AND USE THEREOF IN PHARMACEUTICAL COMPOSITIONS

[75] Inventors: Francesco della Valle, Padua; Aurelio Romeo, Rome, both of Italy

[73] Assignee: FIDIA, S.p.A., Abano Terme, Italy

[*] Notice: The portion of the term of this patent subsequent to Jun. 3, 2003 has been disclaimed.

[21] Appl. No.: 837,201

[22] Filed: Mar. 10, 1986

Related U.S. Application Data

[63] Continuation of Ser. No. 425,462, Sep. 28, 1982, Pat. No. 4,593,091, which is a continuation-in-part of Ser. No. 290,106, Aug. 4, 1981, Pat. No. 4,476,119.

[51] Int. Cl.$^4$ .................. C08B 37/00; C07H 5/04
[52] U.S. Cl. .................... 536/53; 536/1.1; 536/20; 536/55.1; 536/123
[58] Field of Search .............. 536/53, 20, 1.1, 55.1

[56] References Cited

U.S. PATENT DOCUMENTS

| | | | |
|---|---|---|---|
| 4,125,492 | 11/1978 | Cuatrecasas et al. | 536/1.1 |
| 4,225,487 | 9/1980 | Cuatrecasas et al. | 536/1.1 |
| 4,347,244 | 8/1982 | Mynard et al. | 536/1.1 |
| 4,415,733 | 11/1983 | Tayot | 536/53 |
| 4,593,091 | 6/1986 | della Valle et al. | 536/53 |

FOREIGN PATENT DOCUMENTS

| | | |
|---|---|---|
| 0008969 | 3/1980 | European Pat. Off. . |
| 0038265 | 10/1981 | European Pat. Off. . |
| 0072722 | 2/1983 | European Pat. Off. . |

OTHER PUBLICATIONS

Gross et al., Carbohydrate Research, 41 (1975), pp. 344–350.
Biochimica et Biophysica Acta, Shrager et al., 318 (1973), pp. 141–146.
Charles C. Sweeley et al., "Chemistry of Mammalian Glycolipids", pp. 492–504 (1968).
Robert H. McCluer et al., "Ganglioside Inner Esters", pp. 95–102 (1972).
Gross et al., "Journal of Neurochemistry", vol. 28, pp. 1133–1136 (1977).
Takata et al., "Journal of General Physiology", vol. 49, pp. 977–988 (1966).
Narahashi et al., "Journal of General Physiology", vol. 47, pp. 965–974 (1964).
Nakamura et al., "Journal of General Physiology", vol. 48, pp. 985–996 (1965).
Cuervo et al., "Journal of General Physiology", vol. 55, pp. 309–335 (1920).
Hille, "Journal of General Physiology", vol. 51, pp. 199–219 (1968).
Keynes et al., "J. Physiol.", 213, pp. 235–254 (1971).
Kao et al., "J. Physiol.", 180, pp. 50–66 (1965).
Armstrong, "Nature", vol. 242, pp. 459–461 (1973).
Mosher et al., "Science", vol. 144, pp. 1100–1110 (1964).
Tettamanti et al., Biochemica et Biophysica Acta, 296, 160–170 (1973).
Negrin et al., Minerta Medica, 69, 3277–3282 (1978).
Penick et al., Biochemica et Biophysica Acta, 116, 297–287 (1966).
Mukaiyama et al., Chemistry Letters, pp. 49–50 (1976).
Journal of Neurochemistry, 34, No. 6[35], 1351–1361 (Jun. 1980).
Bulletin of Molecular Biology and Medicine, 3, 170–172 (Sep. 1978).

*Primary Examiner*—Ronald W. Griffin
*Attorney, Agent, or Firm*—Birch, Stewart, Kolasch & Birch

[57] ABSTRACT

The present invention relates to a method for preparing inner ester derivatives of gangliosides and pharmaceutical compositions containing such derivatives to be used in treating disorders of the nervous system. The pharmaceutical compositions of the present invention promote nerve regeneration by stimulating nerve sprouting.

11 Claims, No Drawings

METHOD FOR PREPARING GANGLIOSIDE DERIVATIVES AND USE THEREOF IN PHARMACEUTICAL COMPOSITIONS

This application is a continuation of copending application Ser. No. 425,462, now U.S. Pat. No. 4,593,091 which in turn is a continuation-in-part of application Ser. No. 290,106, now U.S. Pat. No. 4,476,119.

The present invention relates to a method for preparing inner ester derivatives of gangliosides and pharmaceutical compositions containing such derivatives. The pharmaceutical compositions of the present invention are used to treat disorders of the nervous system resulting from accidents or diseases which have in some way damaged the nerve tissue.

Gangliosides are a group of glycosphingolipids and have a structure containing a carbohydrate portion to which is linked a ceramide and sialic acid moiety. The carbohydrate portion includes at least one galactose or glucose moiety and at least one N-acetylglucosamine or N-acetylgalactosamine moiety. The general structure of a ganglioside can then be represented by the following formula:

| one mole of a sialic acid | one mole of ceramide<br>at least one mole of galactose or glucose<br>at least one mole of N—acetylglucosamine or N—acetylgalactosamine |
|---|---| where all of the moieties are linked by a glucosidic bond.

Numerous gangliosides have been identified and have been found to be particularly abundant in nerve tissue, especially in brain tissue. Various studies have shown that the most important of the sialic acids found in gangliosides are N-acetyl-neuraminic acid (NANA) and, to a lesser degree, N-glycolylneuraminic acid. Of the numerous gangliosides which have been identified, the following gangliosides, labeled by their international symbols, have been found to exist in significant amounts in ganglioside mixtures extracted from bovine brain tissue:

$G_{DIb}$ (16%)

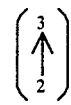

NANA

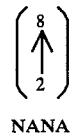

NANA $G_{TIb}$ (19%)

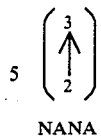

NANA

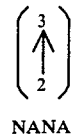

NANA

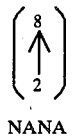

NANA $G_{MI}$ (21%)

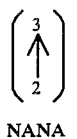

NANA $G_{DIa}$ (40%)

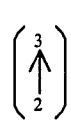 

NANA   NANA where Glc represents glucose, GalNAC represents N-acetylgalactosamine, Gal represents galactose, NANA represents N-acetyl-neuraminic acid and the percentages in parenthesis indicate the amount of each ganglioside found in the ganglioside mixture extracted from bovine brain tissue.

It is known that gangliosides play an important role in the nervous system and it has recently been demonstrated that gangliosides are useful in the treatment of disorders of the peripheral nervous system and pathologies of the central nervous system (Acta psychiat. Scand., 55, 102, (1977); Eur. Med. Phys., 13, 1, (1977); Ric. Sci. Educ. Perm. 9, 115, (1978); Adv. Exp. Biol. 71, 275, (1976); Electromyogr. Clin. Neurophysiol., 19, 353, (1979); Minerva Medica, 69, 3277, (1978); Minerva Stomat., 27, 177, (1978); Med. del Lavoro, 68, 296 (1977); Brain Res. 197, 236, (1980)).

The therapeutic action of the gangliosides appears to consist mainly of stimulating sprouting phenomena in the nerve tissue and in activating the membrane enzymes involved in the conduction of nervous stimuli, such as the enzyme (Na+, K+) ATPase (Brain Res., 197, 236, (1980); Leon et al, J. of Neurochem., 37, 350 (1981)). Nerve sprouting stimulated by the gangliosides will then encourage regeneration and healing of damaged nerve tissue.

OBJECTS AND SUMMARY OF THE INVENTION

Further studies have been directed to finding compounds which may be even more effective than the gangliosides in treating disorders of the nervous system.

It is therefore one object of the present invention to provide a pharmaceutical composition which contains inner ester derivatives of gangliosides and which is effective in treating disorders of the nervous system.

It is another object of the present invention to provide a method for preparing inner ester derivatives of gangliosides.

It is a further object of the present invention to provide a method for treating disorders of the nervous system by administering at least one inner ester derivative of gangliosides.

It is still another object of the present invention to provide a method for treating disorders of the nervous system by administering a mixture of various inner ester derivatives of gangliosides.

It is a still further object of the present invention to provide a method for treating disorders of the nervous system which comprises administering at least one inner ester derivative of gangliosides to promote nerve sprouting in the nerve tissue.

It is another object of the present invention to provide a method for treating disorders of the nervous system which comprises administering at least one inner ester derivative of gangliosides to activate the enzymens involved in conduction of nerve stimuli, such as the enzyme ($Na^+$, $K^+$) ATPase.

These and further objects and benefits of the present invention are accomplished by providing a method for preparing inner ester derivatives of gangliosides and pharmaceutical compositions containing such derivatives to be used in treating disorders of the nervous system. The pharmaceutical compositions of the present invention promote regeneration of damaged nerve tissue by stimulating nerve sprouting.

DETAILED DESCRIPTION OF THE INVENTION

It has now been determined according to the present invention that certain derivatives of gangliosides are more active than the gangliosides themselves in stimulating nerve sprouting and in activating the enzymes of membranes involved in the conduction of the nervous stimulus, such as the enzyme ($Na^+$, $K^+$) ATPase. Specifically, it has been found that the inner ester derivatives of gangliosides are particularly active in treating disorders of the nervous system and are more active than the starting parent gangliosides. In vitro and in vivo testing have shown that the inner ester derivatives are superior to the parent gangliosides in stimulating nerve sprouting and in activating the ($Na^+$, $K^+$) ATPase membrane enzyme involved in nerve conduction.

Only some of the possible inner ester derivatives of the gangliosides have thus far been isolated and these only in very small quantities in brain tissue. The inner esters of gangliosides are formed by the reaction between the carboxyl group of a sialic acid moiety with a hydroxyl group of one of the carbohydrate moieties or another adjoining sialic acid within the same ganglioside molecule (J. of Neurochemistry, 34, 1351, (1980), Bull. of Molecular Biology and Medicine, 3, 170, (1978)). For exemplary purposes, one possible inner ester derivative of a ganglioside could be represented by the following structure:

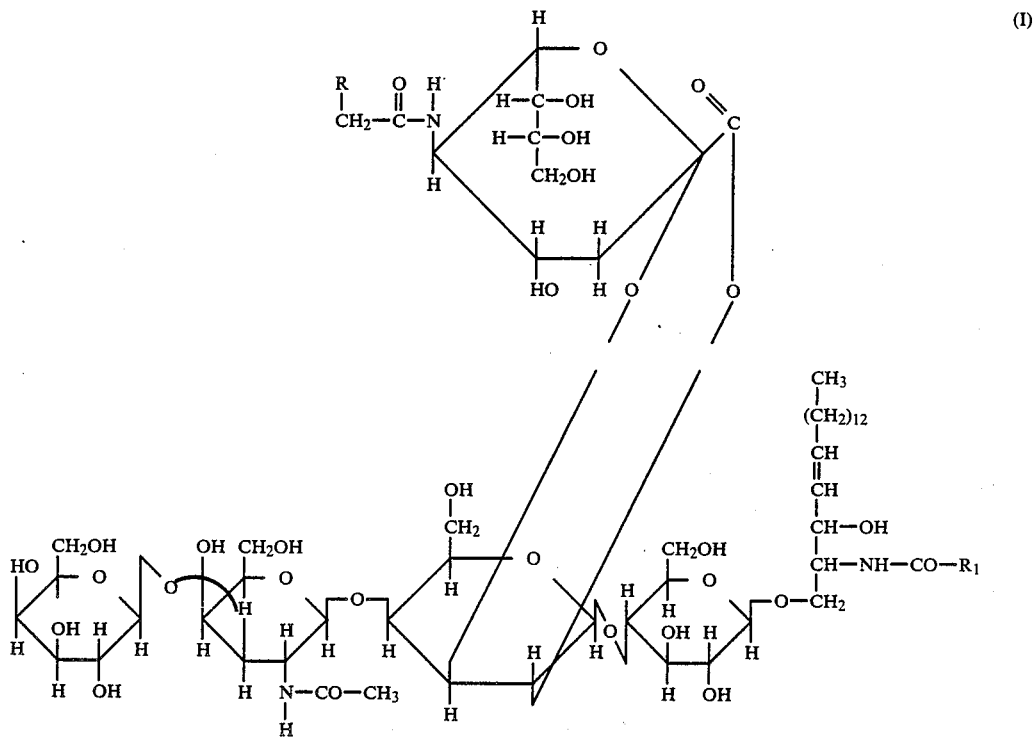

(I)

wherein R in the sialic acid moiety is H or OH and $R_1$ in the ceramide group is a fatty acid such as oleic, stearic or linoleic acid.

The inner ester ganglioside derivative (I) is an example of a derivative in which the carboxyl group of the sialic acid is ester bonded to a hydroxyl group of one of the carbohydrate moieties, specifically galactose. The formation of the inner ester bond, together with the normal glucosidic bond between the sialic acid and carbohydrate moiety, creates a lactonic ring, typically five or six-membered, characteristic of the structure of the inner ester ganglioside derivatives. While Formula I has been shown for exemplary purposes, it is to be noted that other lactonic rings having 5 or more membered ring structures could be formed as the sialic acid carboxyl group ester bonds with the hydroxyl group of a carbohydrate moiety.

As noted above, the inner ester ganglioside derivatives can also be formed when the carboxyl group of a sialic acid ester bonds to an adjoining sialic acid to which it is glucosidically bonded in the starting parent ganglioside. Such a structure could be represented by the following formula:

erally formed of a carbohydrate portion, at least one ceramide and at least one sialic acid moiety wherein one or more of the sialic acids are ester bonded to a carbohydrate moiety and/or one or more of the sialic acids are ester bonded to an adjoining sialic acid. Numerous inner ester derivatives of gangliosides are thus possible, of which the above described are shown for examplary purposes only.

METHOD OF PREPARATION

Some prior art methods for the preparation of inner ester ganglioside derivatives are known and include the following:

1. The formation of internal esters by simply allowing the gangliosides to stand in an acetic or trichloroacetic acid solution (Sphingolipids, Sphingolipidoses and Allied Disorders, Adv. Exp. Med. Biol. 19, 95, (1972); J. Neurochem. 28, 1133, (1977)). According to this method, it is necessary to operate at a very high ratio of acetic acid to ganglioside and a complete transformation of the gangliosides is not obtained. For this reason, a final purification step is necessary and is usually performed by an ion exchange resin, such as Sephadex.

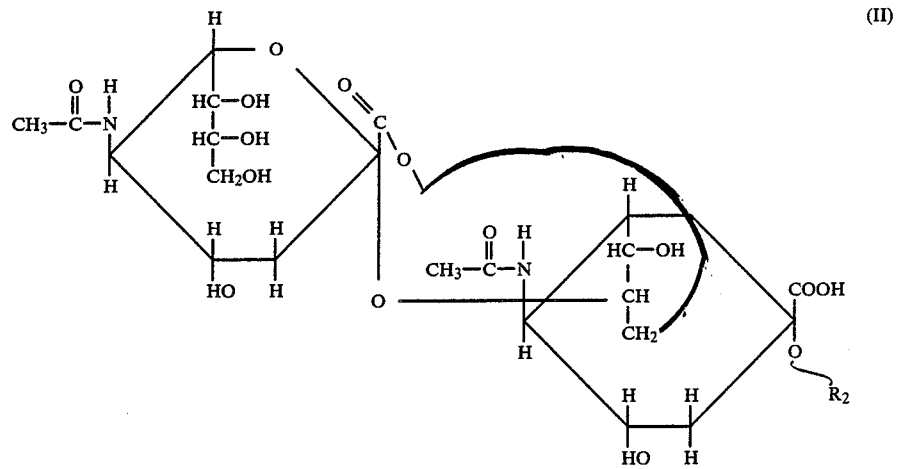

(II)

wherein $R_2$ represents the carbohydrate moiety which is glucosidically linked to the sialic acid moiety.

Another possible inner ester ganglioside derivative could be represented by the following formula:

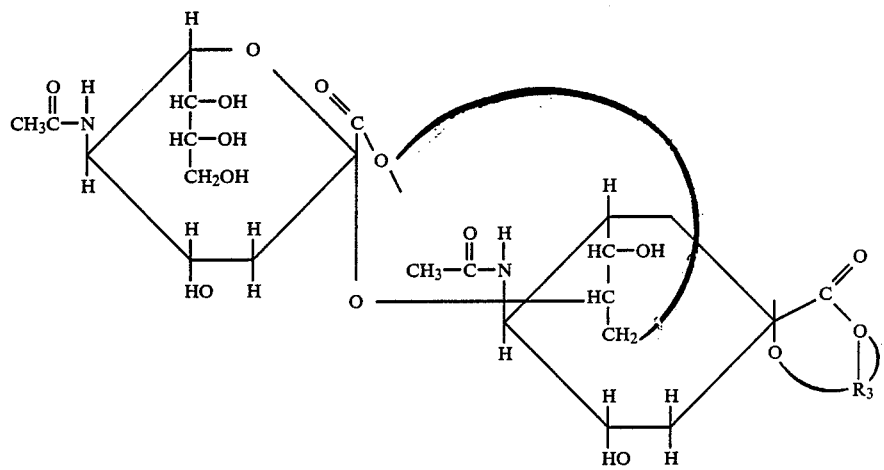

(III)

wherein $R_3$ represents the carbohydrate moiety to which the adjoining sialic acid is ester bonded. Formula III then represents an inner ester ganglioside derivative in which a sialic acid is ester bonded to an adjoining sialic acid which is itself ester bonded to a carbohydrate moiety. It is therefore apparent that many variations of the above described derivatives could be formed, so that the inner ester derivatives of gangliosides are gen- 2. The reaction of a water soluble carbodiimide with gangliosides in an aqueous medium (Carbohydr. Res. 41, 344, (1975)). By this method, a complete transformation of the gangliosides is also not obtained because the reaction is performed in an aqueous medium. Utilization of this method results in very low yields and a final purification of the inner ester product is necessary.

According to the present invention, a new and improved method for preparing inner ester ganglioside derivatives is described whereby high yields of the derivatives are obtained. The method of the present invention comprises reacting gangliosides with a lactonization reagent in a non-aqueous organic solvent under anhydrous conditions. Suitable organic solvents to be used in the present invention include dimethylsulfoxide (DMSO), dimethylformamide (DMF), sulfolane, tetrahydrofuran, dimethoxyethane and pyridine or mixtures thereof. Suitable lactonization reagents include carbodiimides soluble in organic solvents such as dicyclohexylcarbodiimide, benzyllisopropylcarbodiimide and benzylethylcarbodiimide, 2-chloro-1-methyl-pyridinium salts, ethoxyacetylene and Woodward reagent (N-ethyl-5-phenyllisoxazolium-3'-sulfonate). While the prior art methods of reacting gangliosides with a carbodiimide in an aqueous medium result in very low yields of the inner ester derivatives, it has been found that the process of the present invention which comprises reacting gangliosides in a non-aqueous medium, results in very high, that is, substantially quantitative yields of the desired inner ester derivatives in amounts superior to that possible with the prior art methods. The starting ganglioside compounds used in the process of the present invention are extracted from the brain tissue of mammals, most preferably from bovines.

The following examples represent methods according to the present invention for preparing inner ester derivatives of gangliosides.

EXAMPLE 1

A mixture of gangliosides is obtained by extraction from bovine brains and 5 g of this mixture are dissolved in 50 ml of DMSO. Then, 4 g of anhydrous styrene type resin (sulfonic acid)(50–100 mesh, H+ form) are added to the mixture and the resulting system is stirred for 30 minutes at room temperature. This treatment with an ion exchange resin converts all of the ganglioside carboxylate groups to —COOH (carboxyl) groups. Complete conversion of the carboxylate groups is confirmed by an appropriate physical analytical method, such as atomic absorption. The resin is then filtered under suction and the solution is treated with 1.5 g of dicyclohexylcarbodiimide and allowed to stand for one hour. The dicyclohexylurea which precipitates is removed by filtration and the remaining solution is treated with 100 ml of acetone causing precipitation of the product inner ester ganglioside derivatives. The method yields 4.6 g of inner ester product (about 90–95% of the theoretical value).

The presence of the inner ester derivatives is confirmed by infrared spectroscopy and by thin layer chromatography.

IR Spectroscopy—Performed on a KBr pellet, the esterlactone bond produces a band at 1750 cm$^{-1}$.

Thin Layer Chromatography—On silica gel plates, solvent system CHCl$_3$/MeOH/0.3% CaCl$_2$ (55:45:10, v/v/v), the $R_f$ of the mixture of internal esters ranges between 0.7 and 0.85. The $R_f$ of the final products exceeds the $R_f$ of the mixture of the starting compounds. The chromatography results thus show the absence of any starting material. By treatment with a 0.1N solution of Na$_2$CO$_3$ at 60° C. for 1 hour, the ester bonds are cleaved and the original mixture of starting ganglioside compounds can be obtained.

EXAMPLE 2

9 g of a ganglioside mixture (sodium salt) are dissolved in 80 ml of distilled water and passed through a column filled with 20 g of Dowex 50 w×8 (100–200 mesh triethylammonium form).

This product, anhydrified in high vacuum, is dissolved (with the aid of a sonicator bath) in 200 ml of anhydrous tetrahydrofuran containing 8 ml of triethylamine.

This solution is slowly added to 600 ml of anhydrous tetrahydrofuran (4 hours) containing 40 mM of 2-chloro-1-methyl-pyridinium salt (where the anion could be, for example, iodide, toluene-4-sulfonate, trifluoromethane sulfonate, etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 90 ml of chloroform/methanol 1:1 and precipitated in 450 ml of acetone. The product is finally dried in high vacuum.

Yield—7.9 g (89.7% of the theoretical value).

Thin layer chromatography:On silica gel plates, solvent system chloroform/methanol/CaCl$_2$ 0.3%, 55:45:10, the Rf of the mixture of inner esters ranges between 0.7 and 0.85. The Rf of the final products exceeds the Rf of the mixture of the starting compounds. The chromatography results thus show the absence of any starting material. By treatment with 0.1N solution of Na$_2$CO$_3$ at 60° C. for one hour, the ester bonds are cleaved and the original ganglioside compounds can be obtained.

The IR spectrum of the inner or internal esters of the ganglioside mixture, performed on a KBr pellet, shows the typical ester absorption of 1750 cm−1.

EXAMPLE 3

8 g of GM$_1$ (sodium salt) are dissolved in 80 ml of distilled water and passed through a column filled with 10 g of Dowex 50 w×8 (100–200 mesh triethylammonium form).

This product, anhydrified in high vacuum, is dissolved (with the aid of a sonicator bath) in 200 ml of anhydrous tetrahydrofuran containing 4 ml of triethylamine.

This solution is slowly added to 600 ml of anhydrous tetrahydrofuran (4 hours) containing 20 mM of 2-chloro-1-methyl-pyridinium salt (where the anion could be, for example, iodide, toluene-4-sulfonate, trifluoromethane sulfonate etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 80 ml of chloroform/methanol 1:1 and precipitated in 400 ml of acetone. The product is finally dried in high vacuum.

Yield—7.0 g (88.4% of the theoretical value).

Thin layer chromatography: On silica gel plates, solvent system chloroform/methanol/CaCl$_2$ 0.3%, 55:45:10, the Rf of the final product (0.70) exceeds the Rf (0.65) of the starting compound. The chromatography results thus show the absence of any starting material. By treatment with 0.1N solution of Na$_2$CO$_3$ at 60°

C. for one hour, the ester bond is cleaved and the original ganglioside can be obtained.

The IR spectrum of the inner ester of $GM_1$, performed on a KBr pellet, shows the typical ester absorption of 1750 $cm^{-1}$.

EXAMPLE 4

9 g of a ganglioside mixture (sodium salt) are dissolved in 80 ml of distilled water and passed through a column filled with 20 g of Dowex 50 w×8 (100-200 mesh pyridinium form).

This product, anhydrified in high vacuum, is dissolved in 800 ml of anhydrous tetrahydrofuran and 4.2 g (60 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield—8.1 g (92.0% of the theoretical value).

Thin layer chromatography: On silica gel plates, solvent system chloroform/methanol/$CaCl_2$ 0.3%, 55:45:10, the Rf of the mixture of inner esters ranges between 0.7 and 0.85. The Rf of the final products exceeds the Rf of the mixture of the starting compounds. The chromatography results thus show the absence of any starting material. By treatment with 0.1N solution of $Na_2CO_3$ at 60° C. for one hour, the ester bonds are cleaved and the original ganglioside compounds can be obtained.

The IR spectrum of the inner esters of the ganglioside mixture, performed on a KBr pellet, shows the typical ester absorption of 1750 $cm^{-1}$.

EXAMPLE 5

8 g of $GM_1$ (sodium salt) are dissolved in 80 ml of distilled water and passed through a column filled with 10 g of Dowex 50 w×8 (100-200 mesh pyridinium form).

This product, anhydrified in high vacuum, is dissolved in 800 ml of anhydrous tetrahydrofuran and 2.1 g (30 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield—7.2 g (91.0% of the theoretical value).

Thin layer chromatography: On silica gel plates, solvent system chloroform/methanol/$CaCl_2$ 0.3%, 55:45:10, the Rf of the final product (0.70) exceeds the Rf (0.65) of the starting compound. The chromatography results thus show the absence of any starting material. By treatment with 0.1N solution of $Na_2CO_3$ at 60° C. for one hour, the ester bond is cleaved and the original ganglioside can be obtained.

The IR spectrum of the inner ester of $GM_1$ performed on a KBr pellet, shows the typical ester absorption of 1750 $cm^{-1}$.

EXAMPLE 6

9 g of ganglioside mixture (sodium salt) are dissolved in 80 ml of distilled water and passed through a column filled with 20 g of Dowex 50 w×8 (100-200 mesh pyridinium form).

This product, anhydrified in high vacuum and dissolved in 200 ml of anhydrous pyridine, is added to a suspension of 5.52 g (10 mM of the Zwitterionic Woodward reagent (N-ethyl-5-phenylisoxazolium-3'-sulfonate, Woodward et al., J. Am. Chem. Soc. 83, 1010–1012, 1961) in 200 ml of anhydrous pyridine. This reaction mixture is stirred for 10 days at room temperature.

After filtration of the excess reagent and complete removal of the solvent, the residue is dissolved in 90 ml of chloroform/methanol 1:1 and precipitated in 450 ml of acetone.

Yield—7.2 g (81.8% of the theoretical value).

Thin layer chromatography: On silica gel plates, solvent system chloroform/methanol/$CaCl_2$ 0.3%, 55:45:10, the Rf of the mixture of inner esters ranges between 0.7 and 0.85. The Rf of the final products exceeds the Rf of the mixture of the starting compounds. The chromatography results thus show the absence of any starting material, by treatment with 0.1N solution of $Na_2CO_3$ at 60° C. for one hour, the ester bonds are cleaved and the original ganglioside compounds can be obtained.

The IR spectrum of the inner esters of the ganglioside mixture, performed on a KBr pellet, shows the typical ester absorption of 1750 $cm^{-1}$.

EXAMPLE 7

8 g of $GM_1$ (sodium salt) are dissolved in 80 ml of distilled water and passed through a column filled with 10 g of Dowex 50 w×8 (100-200 mesh pyridinium form).

This product, anhydrified in high vacuum and dissolved in 200 ml of anhydrous pyridine, is added to a suspension of 1.26 g (5 mM) of the Zwitterionic Woodward reagent (N-ethyl-5-phenylisoxazolium-3'-sulfonate), in 200 ml of anhydrous pyridine. This reaction mixture is stirred for 10 days at room temperature.

After filtration of the excess reagent and complete removal of the solvent, the residue is dissolved in 80 ml of chloroform/methanol 1:1 and precipitated in 400 ml of acetone.

Yield—6.3 g (79.5% of the theoretical value).

Thin layer chromatography: On silica gel plates, solvent system chloroform/methanol/$CaCl_2$ 0.3%, 55:45:10, the Rf of the final product (0.70) exceeds the Rf (0.65) of the starting compound. The chromatography results thus show the absence of any starting material. By treatment with 0.1N solution of $Na_2CO_3$ at 60° C. for one hour, the ester bond is cleaved and the original ganglioside can be obtained.

The IR spectrum of the inner ester of $GM_1$ performed on a KBr pellet, shows the typical ester absorption of 1750 $cm^{-1}$.

PHARMACOLOGICAL PROPERTIES

While some inner ester derivatives of gangliosides and methods for making such derivatives have been discussed in the prior art, there has been no previous disclosure of biological activity or possible pharmaceutical uses for the inner ester derivatives. However, according to the present invention, it has been found that inner ester ganglioside derivatives have a very high activity in treating disorders of the nervous system and, in fact, have a much higher activity than that of the gangliosides themselves. The inner ester ganglioside derivatives may be used to treat a variety of nerve disorders including peripheral and central nervous system disorders resulting from diseases or accidents. The compounds may also be used in post-operative therapy following surgery which affects the nerves, such as hemorrhoid surgery.

The superior pharmacological properties of the inner ester ganglioside derivatives which are the subject of this invention can be evaluated in comparison with gangliosides by the following tests:

1—Neurite sprouting in pheocromocitoma cell line ($PC_{12}$)
2—Neuronal membrane ($Na^+$, $K^+$) ATPase activity
3—Recovery of the electroretinogramme following dazzling 1. Effect of Inner Ester Ganglioside Derivatives on Neurite Sprouting of $PC_{12}$ Materials and Methods Neurite sprouting may be considered as localized neuronal differentiation and the biochemical mechanism by which the ganglioside molecules produce the above effect can be studied by evaluating an in vitro cell culture model ($PC_{12}$ cell line derived from a 1A subclone supplied by Dr. P. Calissano (C.N.R.—Laboratorio di Biologia Cellurlare—Roma, Italy)) ("Gangliosides in Neurological and Neuromuscular Function, Development and Repair", Ed. by M. M. Rapport and A. Gorio, Raven Press, New York (1981). In this model, the gangliosides or inner ester ganglioside derivatives are added to the $PC_{12}$ culture medium together with the nerve growth factor (NGF), a specific inducer of $PC_{12}$ differentiation to stimulate neurite sprouting. The neurite sprouting stimulated by the gangliosides can then be compared to that stimulated by the inner ester ganglioside derivatives.

Specifically the cells (100,000/plate) were maintained at 37° C. in an Heraeus incubator (5% $CO_2$ and 95% humidified air) and plated in a Collagen-coated tissue culture, 60 mm Integrid Falcon Plates, in the presence of the following culture medium: 85% RPM 1640 (Gibco), 10% heat-inactivated horse serum (Gibco), 5% fetal calf serum (Gibco), 50 U/ml penicillin and 25 mg/ml streptomycin. The medium was changed every 48 hours.

In such conditions, the cells divide but do not form neurites. Addition of NGF (50 mg/ml) causes the cells to cease proliferation, form neurites and differentiate within 5–10 days. This effect was evaluated by counting the number of cells with neurites beginning on day 5 then on every alternate day. The gangliosides and their derivatives (1 mM) were added to the culture medium simultaneously with NGF and their effect was assessed on days 7 and 9 by counting the number of cells containing neurites.

Results

The results of the comparative studies on neurite sprouting are summarized in Table 1.

TABLE 1

Effect of ganglioside derivatives on neurite sprouting in $PC_{12}$ cells

| Compound | Cell Line | Medium | Concentration | % of the number of cells with neurites day 7 | % of the number of cells with neurites day 9 |
|---|---|---|---|---|---|
| Control | $PC_{12}$ | 85% RPM 1640, 10% heat-inact. horse serum, 5% fetal calf serum 50 U/ml penicillin and 25 mg/ml streptomycin. | | 31 | 35.7 |
| ganglio-sides | $PC_{12}$ | 85% RPM 1640, 10% heat-inact. horse serum, 5% fetal calf serum 50 U/ml penicillin and 25 mg/ml streptomycin. | 1 mM | 49.5 | 62.3 |
| inner esters of gangliosides | $PC_{12}$ | 85% RPM 1640, 10% heat-inact. horse serum, 5% fetal calf serum 50 U/ml penicillin and 25 mg/ml streptomycin. | 1 mM | 56.3 | 69.2 |

The results obtained show that the inner ester ganglioside derivatives of the present invention have the capability to stimulate neuronal sprouting and proved to be much more active than gangliosides in producing the effect both in seven days, and in nine days.

2. Effect of Ganglioside Derivatives on the Neuronal Membrane ($Na^+$, $K^+$) ATPase Activity The capability of the gangliosides or inner ester ganglioside derivatives to activate the membrane enzyme ($Na^+$, $K^+$) ATPase can be evaluated in vitro in a neuronal membrane preparation (J. of Neurochem., cited supra).

MATERIALS AND METHODS a. Preparation of the Rat Brain Crude Mitochondrial Fraction ($P_2$ Fraction)

The procedure used for preparing the $P_2$ fraction was derived from that of Morgan et al, Biochem. Biophys. Acta 241, 737 (1971). (All operations were performed at 0°–4° C.; the × g values are average centrifugal forces). Sprague Dawley (from Charles River) adult male rats (150–175 g body weight) were decapitated and their brains rapidly removed and washed in ice-cold isotonic solution. After excision of the cerebellum, the brains were homogenized by 12 up-and-down strokes of a motor-operated Teflon-glass homogenizer (stated radial clearance, 0.25 mm; 800 r.p.m.) using 4 vol. of the homogenizing solution (0.32M sucrose containing 1 mM potassium phosphate buffer and 0.1 nM bisodium EDTA, pH 7.27). The homogenate was diluted to 10% (w/V) in the homogenizing solution, filtered through four layers of cheese cloth, and centrifuged at 1000× g for 15 minutes.

The resulting pellet was washed with the same starting volume of homogenizing solution and centrifuged as above. The combined supernatants were centrifuged at 17,500× g for 25 minutes (these gravitational conditions were employed in order to have the maximal enrichment of nerve endings in the fraction) and the pellet was washed four times with 9 volumes (each time) of homogenizing solution and centrifuged (17,5000× g for 25 min.). The final pellet, referred to as the "$P_2$ fraction" contains, as the major constituents, unruptured mitochondria and nerve endings. The final pellet was homogenously resuspended with an appropriate volume of homogenizing solution with the above Teflon-glass homogenizer and immediately used for assay. In order to avoid inconsistencies associated with storage, fresh P₂ fractions were always prepared prior to use. The P₂ fraction preparations had a ganglioside content of 33.9±2.8 (S.D.) nmoles bound NeuAc/mg protein.

b. ATPase Assay

ATPase activity was measured spectrophotometrically according to Wallick et al (J. Pharm. Exptl. Therap. 189, 434, (1974)). The reaction mixture, unless otherwise stated, consisted of: 50 mM sucrose, 0.2 mM bisodium EDTA (adjusted to pH 7.4), 100 mM NaCl, 5 mM $MgCl_2$, 10 mM KCL, 2 mM phospho(enol) pyruvat monopotassium salt (PEP)(adjusted to pH 7.4), 3 mM ATP, 50 mM TRIS-HCl pH 7.4, 0.33 mM NADH, pyruvate-kinase (PK) (30 μg/ml) and lactate-dehydrogenase (LDH) (10 μg/ml) in a final volume of 3 ml and a final pH of 7.2. The reaction was started by the addition of 50–75 μg (as protein) of P₂ fraction. ($Na^+$, $K^+$) ATPase activity was obtained by the difference between total ATPase and $Mg^{2+}$ dependent ATPase measured in the presence of $3 \times 10^{-5}$ M ouabain. The time required for each individual assay was 3–5 minutes.

ATPase activity was expressed as International Units (IU) (μmoles ATP hydrolyzed/mg protein/min).

The activity of the ganglioside derivatives (50 nM) was assayed following incubation with the neuronal membranes at 37° C. for two hours.

Results

The results of the comparative studies on ATPase activity are summarized in Table 2.

TABLE 2

| | Effect of ganglioside derivatives on the neuronal membrane ($Na^+$, $K^+$)ATPase | | | |
|---|---|---|---|---|
| Group | Incubation time | Incubation temperature | Concentration (nM) | % increase of ($Na^+$, $K^+$) ATPase activity |
| Control | 120 minutes | 37° C. | — | 100 |
| gangliosides | 120 minutes | 37° C. | 50 | 142 |
| inner esters of gangliosides | 120 minutes | 37° C. | 50 | 174 |

The results obtained show that the inner ester ganglioside derivatives of the present invention have the capability to activate the neuronal membrane enzyme ($Na^+$, $K^+$) ATPase and proved to be much more active than gangliosides under the same conditions of molar concentration.

3. Effect of Ganglioside Derivatives on Recovery of the Electroretinogramme Damaged by Dazzling The capability of gangliosides or inner ester ganglioside derivatives to accelerate the recovery of the retinal electrical activity can be evaluated after physical damage (dazzling) in rabbits. In this model, gangliosides or inner ester ganglioside derivatives are administered parenterally (intravenously) ["Int. Symposium on the Neurochemistry of the Retina", Athens, Aug. 28–Sept. 1 (1979) (Communication)] ["Satellite Meeting on Biochemical and Pharmacological Implications of Gangliosides Functions", Cortona, Aug. 28–31 (1975)(Communications)].

METHODS AND MATERIALS

Male New Zealand rabbits weighing between 1.9 and 2 kg were utilized. ("Int. Symp. on the Neurochemistry of the Regina", Athens, Aug. 28–Sept. 1 (1979)).

Corneal anaesthesia was induced by a local application of 0.4% novesine. The electroretinogramme was registered by applying a corneal electrode (according to Henkes) fixed with a mild suction. The reference electrode consisted of a needle inserted subcutaneously into the frontal area.

The following apparatus was used: AC preamplifier 5A22N Tektronics (10 Hz DC filters); Neuroaverager 1172 OTE Biomedica analyzer; XY plotter L800 Linseis recorder; 1273 OTE Biomedica photostimulator.

Photostimulation was carried out with five flashes of 0.2 watts/sec. of 10 sec. of duration and 0.5 Hertz of frequency. Base time for the registration was 100 msec (pre-set=5).

The animals were kept in a dark room for 30 minutes to adapt to darkness in conditions of constant air, temperature and noise.

The following determinations were performed:

1. Three base controls, one every 15 minutes, were evaluated in all animals. The mean of waves a+b (peak to peak) was calculated.

2. The animals were then subjected to dazzling for 20 minutes by utilizing a Schott Mainz KL150B lamp positioned at a distance of 1 cm from the corneal electrode. After this period, the electroretinogramme (ERG) recovery was determined by measuring the amplitude of the ERG at 20, 40 and 60 minutes following the dazzling period. This permitted an assessment of the animals' basal condition to be made.

The animals were subsequently treated with the compounds and 30 minutes later were once again subjected to dazzling and the registration of the ERG took place in identical conditions as mentioned above.

The compounds were administered at 33 nmole/Kg by an intravenous injection.

RESULTS

The results of the comparative studies on electroretinogramme recovery are summarized in Table 3.

TABLE 3

| | Effect of ganglioside derivatives on the electroretinogramme recovery. | | | | |
|---|---|---|---|---|---|
| | | | % ERG recovery in respect to controls | | |
| Compound | Animals | Dosage i.v. | 20 min. | 40 min. | 60 min. |
| gangliosides | Rabbit | 33/nmole/kg | +5 | +9.0 | +13.0 |
| inner esters of gangliosides | Rabbit | 33/nmole/kg | +8 | +12.7 | +20.5 |

The results thus obtained show that the internal ester derivatives of the present invention do increase recovery in electroretinograms and show a larger activity than the gangliosides at all of the examined times.

THERAPEUTIC UTILIZATION

The inner ester ganglioside derivatives of the present invention can be used as drugs for different therapies for treating the nervous system, particularly peripheral nerve disorders and pathologies of the central nervous system. More particularly, the inner ester ganglioside derivatives can be used in the treatment of peripheral nervous system disorders due to traumatic, compressive, degenerative or toxic-infectious causes where the stimulation of nerve regeneration and recovery of neuromuscular function is necessary, and in central nervous system disorders due to traumatic, anoxic, degenerative or toxic-infectious causes where the stimulation of neuronal sprouting is necessary for functional recovery. These disorders have previously been treated by the use of gangliosides; however, the above described tests show that the inner ester derivatives of gangliosides have much greater activity than that of the gangliosides themselves.

The inner ester ganglioside compounds of the present invention can be utilized as drugs in pharmaceutical preparations administered to humans or animals intramuscularly, subcutaneously or intradermally, by intravenous injection or infusion. The preparations can be solutions of the compounds or a lyophilized powder of the compounds in association with one or more pharmaceutically acceptable carriers or diluents, and contained in buffered media at a contained suitable pH and isotonic with physiological fluids. The dosage administered will depend upon the desired effect and upon the desired administration route. For example (which is not limitative) the dosage can be between 0.05 and 5 mg of active compound per kg of body weight by day with a unitary dosage between 0.05 and 2 mg/kg of body weight.

The therapeutic compositions of the present invention are usually prepared with a mixture of different inner ester ganglioside derivatives but could be prepared containing only one isolated active derivative.

For examplary purposes only, Table 4 shows some possible pharmaceutical composition preparations which could be prepared in the form of a solution for treating disorders of the nervous system.

TABLE 4

| Examples of pharmaceutical composition solution for injection | | |
| --- | --- | --- |
| Preparation No. 1 - one ampoule of 2 ml contains: | | |
| active substance | mg | 5 |
| sodium chloride | mg | 16 |
| citrate buffer pH 6 in | ml | 2 |
| distilled pyrogen free water q.s.a | | |
| Preparation No. 2 - one ampoule of 2 ml contains: | | |
| active substance | mg | 50 |
| sodium chloride | mg | 16 |
| citrate buffer pH 6 in | ml | 2 |
| distilled pyrogen free water q.s.a. | | |
| Preparation No. 3 - one vial of 4 ml contains: | | |
| active substance | mg | 100 |
| sodium chloride | mg | 32 |
| citrate buffer pH 6 in | ml | 4 |
| distilled pyrogen free water q.s.a. | | |

The preparations shown in Table 4 can be directly administered to animals or humans by any of the above-described routes. Additionally, the compositions may contain from about 2% to about 50% by weight of active substance.

Again for examplary purposes, Table 5 shows some possible pharmaceutical composition systems which could be prepared for treating disorders of the nervous system. The pharmaceutical composition systems shown in Table 5 are prepared as two vial systems. A first active substance vial is prepared containing from about 10 to about 90% by weight of a lyophilized powder of the active substance together with a pharmaceutically acceptable excipient, such as glycine and mannitol. A second solvent vial is prepared containing the desired amount of solvent, such as sodium chloride and a citrate buffer. Just prior to administration, the contents of the two vials are admixed and the lyophilized active substance powder quickly dissolves to produce an injectable solution. The pharmaceutical composition system, including a first vial containing the lyophilized powder of the active substance, is the preferred pharmaceutical composition of the present invention since the active substance inner ester ganglioside derivatives are more stable in this state as compared to the pharmaceutical composition solution per se.

TABLE 5

| Examples of pharmaceutical composition systems | | |
| --- | --- | --- |
| System No. 1 | | |
| a. one lyophile of 2 ml contains: | | |
| active substance | mg | 5 |
| glycine | mg | 30 |
| b. one solvent ampoule of 2 ml contains: | | |
| sodium chloride | mg | 16 |
| citrate buffer in distilled pyrogen free water q.s.a. | ml | 2 |
| System No. 2 | | |
| a. one lyophile of 3 ml contains: | | |
| active substance | mg | 5 |
| mannitol | mg | 40 |
| b. one solvent ampoule of 2 ml contains: | | |
| sodium chloride | mg | 16 |
| citrate buffer in distilled pyrogen free water q.s.a. | ml | 2 |
| System No. 3 | | |
| a. one lyophile ampoule of 3 ml contains: | | |
| active substance | mg | 50 |
| glycine | mg | 25 |
| b. one solvent ampoule of 3 ml contains: | | |
| sodium chloride | mg | 24 |
| citrate buffer in distilled pyrogen free water q.s.a. | ml | 3 |
| System No. 4 | | |
| a. one lyophile ampoule of 3 ml contains: | | |
| active substance | mg | 50 |
| mannitol | mg | 20 |
| b. one solvent ampoule of 3 ml contains: | | |
| sodium chloride | mg | 24 |
| citrate buffer in distilled pyrogen free water q.s.a. | ml | 3 |
| System No. 5 | | |
| a. one lyophile vial of 5 ml contains: | | |
| active substance | mg | 100 |
| glycine | mg | 50 |
| b. one solvent ampoule of 4 ml contains: | | |
| sodium chloride | mg | 32 |
| citrate buffer pH 6 in distilled pyrogen free water q.s.a. | ml | 4 |
| System No. 6 | | |
| a. one lyophile vial of 5 ml contains: | | |
| active substance | mg | 100 |
| mannitol | mg | 40 |
| b. one solvent ampoule of 4 ml contains: | | |
| sodium chloride | mg | 32 |
| citrate buffer pH 6 in distilled pyrogen free water q.s.a. | ml | 4 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for preparing inner ester ganglioside derivatives which comprises:

(a) subjecting a ganglioside or mixture of gangliosides to ion exchange to convert the carboxylate groups in said gangliosides to a salt thereof;
(b) dissolving the thus prepared salt of a ganglioside or mixture of gangliosides in a non-aqueous organic solvent; and
(c) reacting said salt of a ganglioside or mixture of gangliosides with a lactonization reagent to form at least one lactonic bond in said inner ester ganglioside derivatives.

2. The method of claim 1, wherein the ganglioside or mixture of gangliosides of step (a) is extracted from bovine brains.

3. The method of claim 1, wherein said organic solvent is selected from the group consisting of dimethyl sulfoxide, dimethylformamide, sulfolane, tetrahydrofuran, dimethoxyethane and pyridine.

4. The method of claim 1, wherein said lactonization reagent is selected from the group consisting of carbodiimides soluble in organic solvents, 2-chloro-1-methyl-pyridinium salts, ethoxyacetylene and N-ethyl-5-phenylisoxazolium-3'-sulfonate.

5. The method of claim 4, wherein the carbodiimide is dicyclohexylcarbodiimide, benzylisopropylcarbodiimide or benzylethylcarbodiimide.

6. The method of claim 4, wherein said inner ester ganglioside derivatives are obtained by precipitation with acetone after said reaction with a lactonization reagent.

7. The method of claim 1, wherein said salt is a tertiary nitrogen salt.

8. The method of claim 1, wherein said salt is a salt with triethylammonium.

9. The method of claim 1, wherein said salt is a salt with pyridinium.

10. The method of claim 1, wherein said ion-exchange resin is in a triethylammonium form.

11. The method of claim 1, wherein said ion-exchange resin is in a pyridinium form.

* * * * *